United States Patent [19]

Williams

[11] Patent Number: 5,036,423
[45] Date of Patent: Jul. 30, 1991

[54] ADJUSTABLE METAL ANTISTATIC BRACELET

[75] Inventor: Eric A. Williams, West Covina, Calif.

[73] Assignee: Desco Industries, Inc., Walnut, Calif.

[21] Appl. No.: 516,423

[22] Filed: Apr. 30, 1990

[51] Int. Cl.⁵ .............................................. H05F 3/02
[52] U.S. Cl. ................................... 361/212; 361/220; 439/92; 174/55 B; 24/265 BC
[58] Field of Search .................... 439/92, 37, 799; 128/796; 174/55 B; 361/212, 220, 223, 224; 24/68 E, 68 J, 265 A, 265 BC, 265 EC, 265 WS

[56] References Cited

U.S. PATENT DOCUMENTS

| | | | |
|---|---|---|---|
| 1,760,913 | 6/1930 | Otten | 24/573.1 |
| 2,588,655 | 3/1952 | O'Neill | 24/71 |
| 3,685,106 | 8/1972 | Gandelman | 24/265 |
| 3,857,397 | 12/1974 | Brosseau | 128/384 |
| 4,096,688 | 6/1978 | Rieth | 59/79 R |
| 4,296,532 | 10/1981 | Ho | 24/206 R |
| 4,373,175 | 2/1983 | Mykkanen | 361/220 |
| 4,375,713 | 3/1983 | Bert et al. | 24/206 R |
| 4,375,713 | 3/1983 | Bert et al. | 24/206 R |
| 4,398,277 | 8/1983 | Christiansen et al. | 361/220 |
| 4,402,560 | 9/1983 | Swainbank | 339/11 |
| 4,459,633 | 7/1984 | Vandermark | 361/220 |
| 4,475,141 | 10/1984 | Antonevich | 361/220 |
| 4,577,256 | 3/1986 | Breidegam | 361/220 |
| 4,639,825 | 1/1987 | Breidegam | 361/212 |
| 4,662,695 | 5/1987 | Gordon et al. | 339/14 R |
| 4,745,519 | 5/1988 | Breidegam | 361/220 |
| 4,755,144 | 7/1988 | Gordon et al. | 439/37 |
| 4,782,425 | 11/1988 | Breidegam | 361/212 |
| 4,816,964 | 3/1989 | Weiss | 361/220 |
| 4,845,585 | 7/1989 | Weiss | 361/220 |

OTHER PUBLICATIONS

Drawing Showing Prior Art Long Used in the Industry.

Primary Examiner—A. D. Pellinen
Assistant Examiner—Richard T. Elms
Attorney, Agent, or Firm—Poms, Smith, Lande & Rose

[57] ABSTRACT

An adjustable metal antistatic bracelet having a metal-link expansion wristband. A metal connector channel connects the ends of said wristband together, there being an end flange at each channel end and which extends into a gap between lower links. At one wristband end, tangs hold down an endmost link so that the end flange remains in a gap. At the other end, different types of means operate selectively to hold the end flange in a gap. An insulating cover snaps onto the channel, and incorporates a grounding stud and means to electrically connect the stud to the channel.

11 Claims, 2 Drawing Sheets

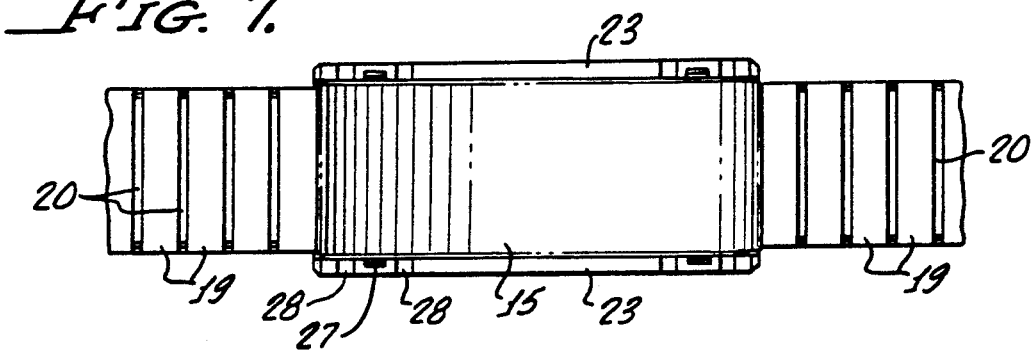
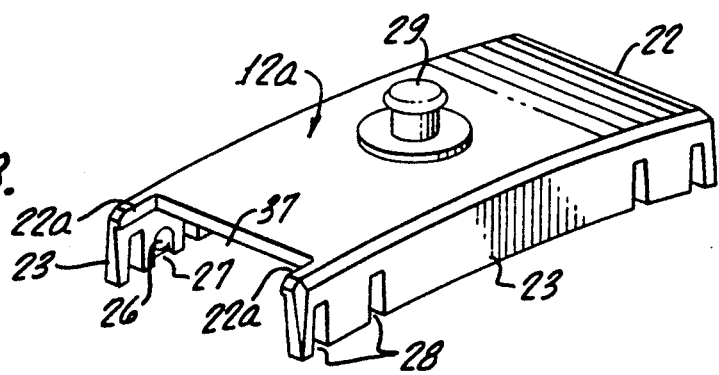
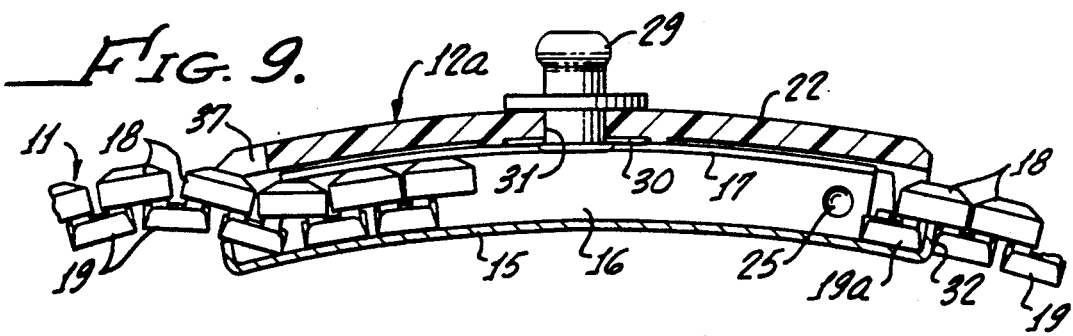
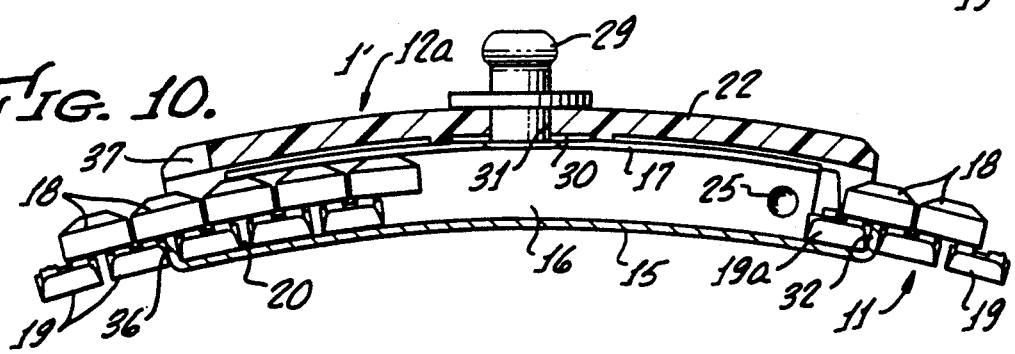

ADJUSTABLE METAL ANTISTATIC BRACELET

BACKGROUND OF THE INVENTION

There has for years existed an industry of providing bracelet devices to electrically ground—through a grounding circuit—certain workers in the field of semiconductor components and circuits. This prevents the static electricity, generated by the workers, from damaging the components or circuits being worked on. A complete grounding circuit is described and illustrated in U.S. Pat. No. 4,373,175, which is hereby incorporated by reference herein.

Two types of bracelets are conventionally made by manufacturers in the indicated field. One employs conductive fibrous material, woven or otherwise, as the band or strap portion of the bracelet. The other employs an expansible metal-link wristband component. The present invention relates to the latter type of device.

At the present time there are approximately five American manufacturers of antistatic bracelets incorporating expansible metal-link wristbands. Such manufacturers buy individual wristbands from Textron Inc. of Providence, R.I. Textron manufactures the wristbands under patents including U.S. Pat. Nos. 4,096,688 and 4,375,713, that are hereby incorporated by reference herein.

The particular metal-link band material now primarily employed in the indicated antistatic industry may be obtained from Textron under its number 01802561, being designated "STATIC SKEL", and trademarked SPEIDEL. The last-indicated component is specially made by Textron for the antistatic bracelet industry, and includes an upper layer of metal links to which is laminated a thin film or sheet of polyvinylfluoride synthetic resin, thus providing insulation to protect the wearer. It is emphasized that the wearer should be protected against electric shock, and this is done, relative to the indicated bracelet or wristband material, by effectively insulating the upper layer of metal links.

The American companies in the metal wristband industry buy the individual wristbands from Textron in three discrete sizes—small, medium and large. At each end of each wristband is a metal loop or hollow cylinder. The companies employ these metal loops to secure the wristbands in nonadjustable manner to opposite ends of a connector element.

It follows that each bracelet manufacturer (and distributors therefor) must stock three sizes of the bracelets, so that they are readily available to the customer. It is also pointed out that "small-medium-large" leaves a great deal to be desired relative to comfort to the user. For certain sizes of wrists, "small" may be somewhat small while "medium" may be somewhat large. Furthermore, the user may desire that different sizes be employed at different times, for example when the temperature changes or when the worker is in different states of mind.

SUMMARY OF THE INVENTION

The present invention eliminates the need for buying the metal-link antistatic wristbands in the three stated sizes. Instead, the wristbands may be bought in large rolls and then cut into same-length sections. These sections are then quickly and easily connected to a connector member. One end of each wristband section is fixed relative to the connector member, while the other end of each section is adjustable to a wide variety of settings relative to the connector member.

In one embodiment bracelet-size adjustment is effected, by the ultimate user, by snapping off a synthetic resin cap, then making the adjustment, and then snapping the cap back on.

In another embodiment, the adjustment may be made without moving or removing the cap. This form of the invention is the best mode contemplated by the inventor.

BRIEF DESCRIPTION OF THE DRAWINGS

FIG. 7 is a fragmentary bottom plan view of the upper part of the bracelet, in free condition as distinguished from stretched condition;

FIG. 8 is an isometric view of the cap of the second embodiment of the invention;

FIG. 9 is a view corresponding to part of FIG. 3 but incorporating the cap of FIG. 8, the adjustable end of the wristband being shown as being inserted into the connecting element while the cap is in mounted condition; and FIG. 10 is a view corresponding to FIG. 4 but showing the connecting element and associated wristband ends in fully operative condition.

EMBODIMENT OF FIGS. 1-6

Figure 1:
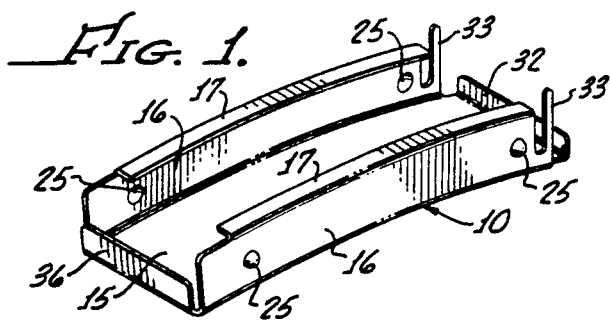
FIG. 1 is an isometric view of the channel which forms the connector between opposite ends of the metal-link wristband.

The adjustable metal-link antistatic bracelet of the first embodiment comprises a connector member 10, an expansible and contractible resilient wristband 11, a cap or cover 12; and electrical connection means 13.

Referring first to connector member 10, this is a channel-shaped backplate preferably formed of stainless steel. It makes electrical contact with the skin of the wearer, who is normally a worker in a plant where electronic components or circuits are made. The channel has a web 15 that is somewhat upwardly concave (on its bottom side) so as to conform to the wrist. It also has side flanges 16 that extend vertically upwardly from web 15. Each side flange 16, in turn, has inwardly-bent edge flanges 17 that are parallel to web 15, such edge flanges extending inwardly for only a relative short distance that is sufficient to hold down the wristband 11.

The wristband 11 is preferably that identified above, being No. 01802561 and called by the manufacturer a continuous coil anti-static metal expansion wristband material. It has an upper layer of substantially parallel upper links 18, and also has a lower layer of substantially parallel lower links 19. The upper links 18 are coated with the insulating synthetic resin as stated above; on the other hand, the links 19 on the lower layer are not insulated but are instead in electrical contact with web 15 and with the wrist of the wearer.

Figure 4:
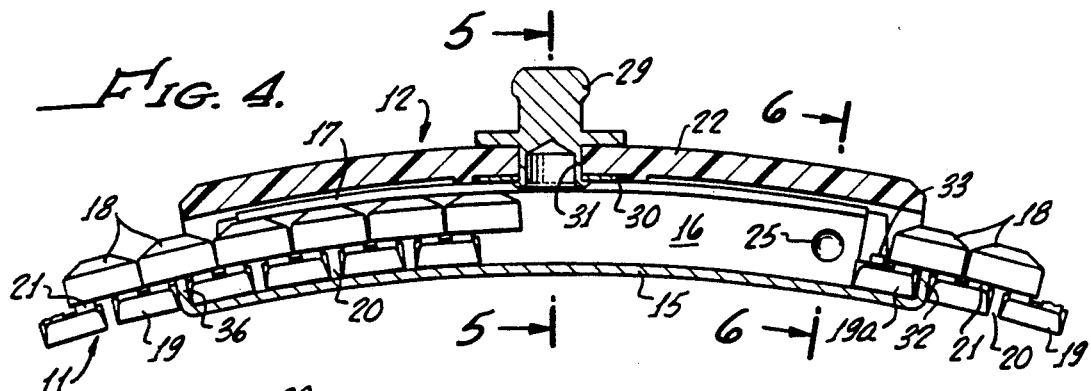
FIG. 4 is an enlarged view of the connector assembly, the cap being shown after it has been snapped into mounted condition on the channel, the wristband ends being shown in mounted and adjusted conditions.

As best shown in FIG. 4, the upper layer of links is offset relative to the lower layer thereof, so that each link bridges the gap between two adjacent links in the other layer. When the wristband is not expanded, the upper links are in engagement with each other while the lower links are spaced slightly apart as shown in FIGS. 4 and 7. Thus, even while the wristband is not at all stretched but instead is in its free condition, there are gaps 20 between each two adjacent lower links 19. As is well known in the art, the constructions described at the beginning of this specification incorporate links that are resiliently connected to each other by assemblies that include small arms 21 some of which are indicated in FIG. 4.

Referring next to cap 12, this comprises—in the preferred embodiment—a resilient cap or cover formed of synthetic resin. The preferred synthetic resin is a resilient ABS (acrylonitrile-butadiene-styrene copolymer). It may also be glass-filled nylon, for example. Cover or cap 12 has a web 22 that is upwardly concave (on its bottom side) correspondingly to channel web 15. The cap also has downwardly-extending side flanges 23 that nest relatively closely over the exterior surfaces of channel flanges 16, reference being made to FIGS. 5 and 6.

Figure 6:
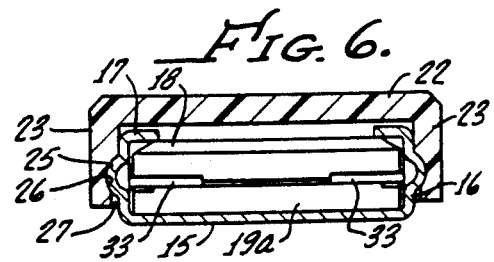
FIG. 6 is a transverse sectional view on line 6—6 of FIG. 4.

In the preferred embodiment, the cap or cover 12 snaps on and off the channel flanges, and this may be done manually by the ultimate user of the bracelet. To hold the cap on the channel, four protuberances or dimples 25 are formed in side flanges 16 near the outer ends thereof, such dimples extending outwardly as shown in FIG. 6. At the dimples 25, side flanges 23 have recesses 26 into which the dimples snap in detent relationship. To increase the ease of mounting the cover on the channel, the bottom regions of recesses 26 communicate with shallow channels that extend downwardly to the edges of side flanges 23, reference being made to FIGS. 3 and 6. Each such channel is sufficiently large to receive at least the outer region of a dimple 25.

To increase the resilience of the cap or cover flanges 23 in the regions of the dimples 25, vertical slots 28 are provided on both sides of each recess 26, reference again being made to FIG. 3. Thus, the flange regions between the slots readily move outwardly and inwardly so that the cap may be snapped on and off. However, the resilience is sufficiently great to maintain the cap in mounted position at all desired times.

Figure 5:
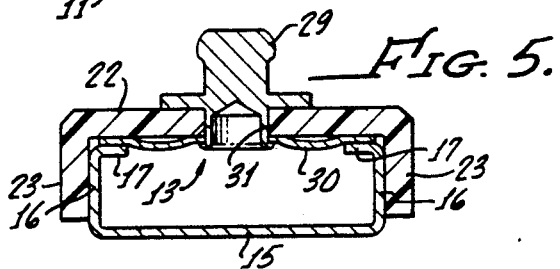
FIG. 5 is a transverse sectional view on line 5—5 of FIG. 4.

Referring next to a description of the electrical connection means 13, this comprises a machined stainless-steel snap stud 29 that is adapted to be snap-connected to a socket member that is suitably grounded, reference being made to the above-indicated U.S. Pat. No. 4,373,175. A stainless-steel spring clip 30 is mounted transversely of the underside of web 22 of the cap or cover, as shown in FIG. 5, this being preferably effected by a rivet 31 forming part of the stud 29. The rivet extends through flange 22 and through the spring clip 30 at the center of the unit.

Clip 30 is sufficiently long, and has square ends, so that it cannot turn substantially about its axis, instead remaining in the desired transverse position shown in FIG. 5. The end portions of the clip resiliently tend to move in downward directions (FIG. 5), so that the ends of the clip resiliently engage the upper surfaces of edge flanges 17 of the channel. Thus, there is effective electrical connection from the ground wire to stud 29, thence to the spring clip 30, thence to flanges 17, thence to web 15, and thence to the undersides of the resilient wristband at both ends thereof. There is thus electrical contact with the wrist of the wearer both through the channel web 15 and through the undersides of the lower links 19.

Figure 2:
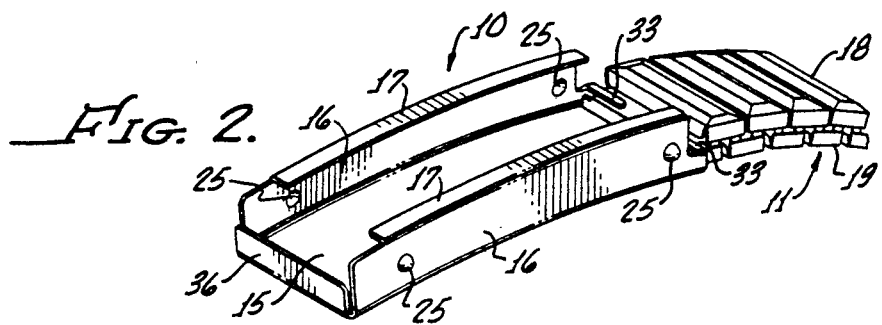
FIG. 2 corresponds to FIG. 1 but shows how one end of the wristband is permanently connected to one end of the channel.

There will next be described the means for connecting one end of wristband 11 fixedly to one end of the connector 10. Referring to the right end portions of FIGS. 1 and 2, the right ends of flanges 16,17 are cut back in relation to the right end of web 15. Such right web end is bent upwardly to form a connector flange 32 that is substantially perpendicular to web 15 and that has a height somewhat greater than that of each lower link 19 of the wristband. In addition, tangs 33 are formed integrally with the channel 10 and extend upwardly from web 15 near the right ends of flanges 16 as viewed in FIG. 1. The tangs 33 are spaced somewhat from, and are parallel to, the right vertical edges of flanges 16.

As previously stated, the wristband material 11 is preferably bought by the bracelet manufacturer in a large roll. Then, at the antistatic bracelet factory, the wristband is cut into identical lengths (there being no necessity for small, medium and large). As shown at the right in FIG. 3, the leftmost lower link 19 is shown at 19a. The right portion (FIG. 3) of this link 19a is directly beneath the leftmost upper link 18; however, the left portion of the lower link 19a protrudes toward the left from such leftmost upper link. The leftward-protruding portion of the link 19a is directly adjacent the tangs 33, the latter be so located for that such result will occur upon assembly.

To make the fixed connection, after the uniform-length wristband section has been cut, the leftmost link 19a is disposed at the right end (FIG. 3) of the channel web 15, and the connector flange 32 is caused to be in the gap 20 between link 19a and the lower link adjacent thereto. Then, both of the tangs 33 are bent downwardly and inwardly, to the positions shown in FIGS. 2, 4 and 6, so as to hold the leftmost link 19a down at its position adjacent web 15. The cooperative action of tangs 33 and flange 32 therefore effectively and economically holds one end of the wristband 11 in the desired position, without any need for a special connector associated with the wristband end at the wristband factory.

Although the link 19a and the tangs 33 are exposed during the indicated assembly operation, the danger of electrical shock during actual use of the bracelet is eliminated or minimized because the insulating cap 12 is snapped downwardly onto channel 10 before the bracelet is put into operation. As shown at the right end of FIG. 4, the right end of cap 12 extends well over the leftmost upper link 18, which has an insulating coating as stated above. The metal elements 19a and 33 are not insulated since they are covered by the insulating cap.

Means are provided to adjustably connect the remaining end of wristband 11 to the remaining end of connector or channel 10. This comprises a connector flange 36 that is bent upwardly from the left end (FIGS. 1 and 2) of channel web 15. Flange 36 is at a right angle to such web, and extends upwardly for a distance preferably slightly larger than the height of each lower link 19.

Figure 3:
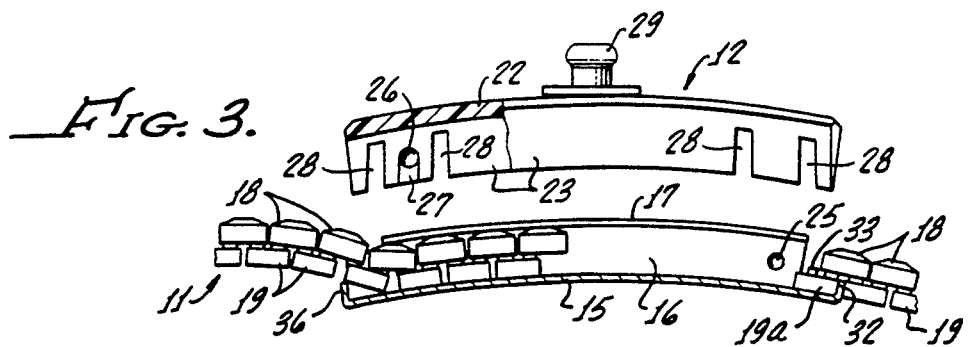
FIG. 3 is a partially exploded longitudinal view, partially in vertical section and partially in side elevation, showing at the right the fixed connection between the wristband and the channel, at the left the wristband during insertion thereof to a desired adjusted position, and at the top a cap which snaps into position after adjustment is completed.

The inwardly-bent edge flanges 17 do not extend all the way to flange 36 or to the left ends (FIGS. 1 and 2) of vertical side flanges 16, being instead cut back substantially therefrom. This cut-back distance is at least sufficient to permit the wristband end to be fed over flange 36 and below edge flanges 17 as shown in FIG. 3, this occurring prior to mounting of the cap or cover 12 on the channel.

To connect the wristband end to connector 10 in a desired adjusted relationship, the wristband end is fed over flange 36 and below flanges 17, as stated, for a desired distance. Then, the wristband end portion is bent downwardly to the FIG. 4 position so that flange 36 penetrates into the space 20 between two adjacent lower links. The number of links fed into the channel may vary between one and many, depending upon the desired bracelet size.

After the wristband end has been fed into the channel to the desired extent, and bent downwardly to the position shown in FIG. 4, the cap or cover 12 is snapped over the channel 10 by means of the above-described detent protuberances or dimples 25 and the associated recesses 26 and channels 27. The left end portion of the cover (FIG. 4) is thereby positioned over the channel end, and the cap effectively holds the wristband down on the connector flange 36 so that no adjustment can be made until the cap is removed. Accordingly, the bracelet has a fixed adjusted condition, but one which may be changed by first removing the cap and then moving the left wristband end (FIGS. 3 and 4) to cause flange 36 to penetrate into a different gap 20 between lower links.

EMBODIMENT OF FIGS. 7-10

This is the preferred embodiment of the invention, the best mode contemplated by the inventor at this time.

Except as stated below, the construction of the embodiment described relative to FIGS. 7-10 is identical to that described relative to FIGS. 1-6.

It has now been discovered that the web 22 of the cap or cover 12a may be cut substantially back away from the connector flange 36, and adjustment easily achieved, without significant loss of the ability of the antistatic bracelet to remain in the desired assembled relationship, and without loss of ability to insulate the wearer from external electrical elements with which contact is not desired. In the present embodiment, adjustment of bracelet size is effected without at any time moving or removing the cap 12a. Instead, as shown in FIG. 9, the wristband is bent upwardly above flange 36, and fed into the channel or out of it, through the gap that remains due to the stated cutting-back of the left end of web 22 of the cap. This gap is numbered 37, being shown by the isometric view of FIG. 8. Preferably, the gap 37 is just barely deep enough that the wristband end portion may be fed in and out of the channel without at any time removing or moving the cap. (The use of the words "cut back" does not imply that the entire cap 12a is not formed by molding.)

After the desired adjustment, the wristband is bent downwardly until connector flange 36 penetrates into a gap 20 between two adjacent bottom links 19, and the adjustment operation is completed. The resilience of the wristband 11 itself, and the closed-loop shape of the wristband, are such as to keep the connector flange 36 in the desired gap 20 so as to maintain the desired assembled operative relationship.

The cutting back of the cap 12a to form the gap 37 does not eliminate the ability of the present electrostatic bracelet to insulate the wearer from exterior electrical components. This is because, as shown in isometric FIG. 8, the left ends of the flanges 23 of the cap or cover 12 cooperate with small remaining portions 22a of web 22. Portions 22a extend horizontally over the left ends of channel side flanges 16 and therefore prevent or minimize the chance of contact of such flanges with exterior electrical elements.

It is pointed out that the gap 37 is not so wide as to expose the left ends of the inwardly-bent channel edge flanges 17, so that these flanges also are effectively prevented from contact with exterior electrical elements. The gap 37 is just sufficiently wide to permit the wristband end portion to feed in and out therethrough with no need to move cap 12a.

With the present embodiment of the invention, adjustment in wristband length made be made in a matter of a few seconds, or even a second, while the cap or cover 12 remains in position.

The foregoing detailed description is to be clearly understood as given by way of illustration and example only, the spirit and scope of this invention being limited solely by the appended claims.

What is claimed is:

1. An adjustable metal antistatic bracelet, which comprises:
   (a) a connector member shaped to be disposed on the wrist of a wearer wearing the antistatic bracelet,
   (b) an expansible and contractible wristband having a lower layer of lower links that are generally parallel to each other and extend transversely to the direction of expansion of said wristband,
      each two adjacent ones of said lower links having a gap therebetween into which flange means may be upwardly extended,
         said lower links being electrically conductive, the links of said wristband being resiliently connected to each other,
   (c) means to connect one end of said wristband to one end of said connector member,
   (d) means to connect the other end of said wristband adjustably to the other end of said connector member,
      said last-named means comprising flange means on said other end of said connector member and shaped to extend upwardly into one of said gaps between said lower links,
         the degree of tightness or looseness of said wristband depending on the one of said gaps into which said flange means is extended,
   (e) means to hold down said wristband at a location sufficiently close to said flange means that said flange means will tend strongly to remain in whichever of said gaps it is extended into,
   (f) cap or cover means mounted over said connector member,
      said cap or cover means and an outer side of the wristband being electrically insulating, to thus minimize the chances of undesired electrical contact between an external object and a wearer wearing said wristband,
         said cap or cover means having an electrical connector stud thereon for connection to a grounding lead, and
   (g) means to electrically connect said stud to said lower links.

2. The invention as claimed in claim 1, in which said hold-down means comprises a portion of said cap or cover means that is spaced away from said flange means, the amount of spacing being sufficiently small that the forces present in said wristband will maintain said flange means extended upwardly into said gap, the amount of said spacing being sufficiently large that, without moving said cap or cover means, a portion of said wristband may be fed over said flange means to cause different ones of said gaps to be registered with said flange means, whereby to adjust the effective length of said wristband.

3. The invention as claimed in claim 1, in which said cap or cover means is movable, and in which said hold-down means comprises a portion of said cap or cover means, said portion being located substantially directly over said flange means and preventing wristband adjustment until said cap or cover means is moved.

4. A metal-link antistatic bracelet, which comprises:
 (a) a connector member shaped to be disposed on the wrist of a wearer wearing the antistatic bracelet,
 (b) a length of antistatic expansion wristband, said wristband having an upper layer of metal links and a lower layer of metal links,
  all of said links being substantially perpendicular to the direction of wristband expansion,
  the links in said upper layer having an electrically insulating coating thereon,
  the links in said upper layer being offset relative to the links in said lower layer,
  said links in said lower layer having gaps therebetween into each of which flange means may be upwardly extended,
 (c) means to connect the ends of said wristband to opposite ends of said connector member,
  said last-named means comprising flange means extending upwardly into one of said gaps between said lower links,
  said last-named means further comprising one of said lower links that is immediately adjacent said one gap into which said flange means extends,
  said one lower link being an endmost lower link on said wristband,
  said last-named means further comprising two metal tangs formed on said connector member adjacent said one lower link,
  said tangs being bent down so as to overlie said one lower link and hold it down so that said flange means remains in said one gap,
 (d) a cap or cover provided over said connector member,
  said cap being electrically insulating,
   said cap having an electrical connector member thereon for electrical connection to a grounding lead, and
 (e) means to electrically connect said electrical connector member to said lower links.

5. An adjustable metal antistatic bracelet, which comprises:
 (a) an elongate connector member formed of metal,
  said member being channel shaped and having a web adapted to be disposed on the wrist of a wearer wearing the bracelet,
  said member also having side flanges extending upwardly from said web,
  said member also having edge flanges extending inwardly from the edges of said side flanges that are remote from said web,
  said member also having at least one end flange extending upwardly from an end portion of said web,
   said end flange being generally perpendicular to said side flanges,
   said end flange being spaced a predetermined distance, longitudinally of said connector member, away from those ends of said edge flanges that are nearest said end flange,
 (b) an expansible and contractible wristband having a lower layer of lower links that are generally parallel to each other and extend transversely to the direction of expansion of said wristband,
  each two adjacent ones of said lower links having a gap therebetween into which said end flange may be upwardly extended,
  said lower links being electrically conductive, the links of said wristband being resiliently connected to each other,
  the amount of spacing of said end flange from said edge flanges being so correlated to the cross-sectional size of said wristband that one end portion of said wristband may be fed over said end flange and into said channel beneath said edge flanges,
  said end portion then being bent down so that said end flange extends into one of said gaps between lower links,
 (c) an electrically insulating cap or cover mounted on said channel and covering said edge flanges,
  the upper links in said wristband being exteriorly electrically insulating,
  said cap having an electrical connector stud thereon for connection to a grounding lead,
 (d) means to electrically connect said stud to said lower links, and
 (e) means to connect the other end of said wristband to the remaining end of said channel.

6. The invention as claimed in claim 5, in which the mounting means for said electrically insulating cap are such that said cap may be manually moved to a position at which said edge flanges are exposed, and in which means are provided to secure said insulating cap in closed position covering said edge flanges and the remainder of said channel.

7. The invention as claimed in claim 6, in which snap-connection means are provided between said side flanges of said channel and portions of said insulating cap, said last-mentioned portions being nested over said side flanges.

8. The invention as claimed in claim 5, in which said insulating cap is recessed back at one end thereof to thus provide a wristband-inlet opening, such that said one end portion of said wristband may be fed through said opening into said channel without moving said cap, an end of said cap being spaced from said end flange sufficiently far to permit insertion of said one end portion of said wristband, said cap end being sufficiently close to said end flange to cooperate with the resilient forces present in said wristband in maintaining said wristband in such position that said end flange is disposed in the desired one of said gaps.

9. The invention as claimed in claim 5, in which one end of said cap is substantially directly over said end flange when said cap is in mounted position on said channel, whereby said one cap end positively maintains said wristband mounted on said end flange with said end flange in the desired gap.

10. The invention as claimed in claim 5, in which said means to electrically connect said stud to said lower links comprises a metal clip mounted on the underside of said cap and connected to said stud, said clip being so disposed that portions thereof seat on said edge flanges when said cap is in mounted condition on said channel, said edge flanges being electrically connected to the web of said channel and thence to said lower layer of links.

11. The invention as claimed in claim 5, in which said means to connect the other end of said wristband to the remaining end of said channel comprises a second end flange provided on said channel at the end portion thereof remote from said first-mentioned end flange, said second end flange being substantially parallel to said first-mentioned end flange, and being adapted to extend into the gap between an endmost lower link in said wristband and the lower link adjacent thereto, and in which two metal tangs are formed on said channel adjacent said endmost lower link, said tangs being bent down to overlie said endmost lower link and hold the same down so that said second end flange remains in said last-named gap.

* * * * *